United States Patent
Hie et al.

(10) Patent No.: US 11,450,439 B2
(45) Date of Patent: Sep. 20, 2022

(54) REALIZING PRIVATE AND PRACTICAL PHARMACOLOGICAL COLLABORATION USING A NEURAL NETWORK ARCHITECTURE CONFIGURED FOR REDUCED COMPUTATION OVERHEAD

(71) Applicants: Brian Hie, Cambridge, MA (US); Bonnie Berger Leighton, Newtonville, MA (US); Hyunghoon Cho, Cambridge, MA (US)

(72) Inventors: Brian Hie, Cambridge, MA (US); Bonnie Berger Leighton, Newtonville, MA (US); Hyunghoon Cho, Cambridge, MA (US)

( * ) Notice: Subject to any disclaimer, the term of this patent is extended or adjusted under 35 U.S.C. 154(b) by 14 days.

(21) Appl. No.: 16/235,606

(22) Filed: Dec. 28, 2018

(65) Prior Publication Data

US 2019/0311813 A1 Oct. 10, 2019

Related U.S. Application Data

(63) Continuation-in-part of application No. 16/020,058, filed on Jun. 27, 2018, now Pat. No. 10,910,087.

(60) Provisional application No. 62/611,678, filed on Dec. 29, 2017.

(51) Int. Cl.
| | |
|---|---|
| *G16H 80/00* | (2018.01) |
| *G16H 10/40* | (2018.01) |
| *G06N 20/00* | (2019.01) |
| *G16C 20/90* | (2019.01) |
| *G16C 20/70* | (2019.01) |
| *G06Q 50/00* | (2012.01) |
| *G16C 20/50* | (2019.01) |
| *G16B 15/30* | (2019.01) |

(52) U.S. Cl.
CPC ............ *G16H 80/00* (2018.01); *G06N 20/00* (2019.01); *G16C 20/90* (2019.02); *G16H 10/40* (2018.01); *G06Q 50/00* (2013.01); *G16B 15/30* (2019.02); *G16C 20/50* (2019.02); *G16C 20/70* (2019.02)

(58) Field of Classification Search
None
See application file for complete search history.

(56) References Cited

U.S. PATENT DOCUMENTS

| | | |
|---|---|---|
| 10,910,087 B2 | 2/2021 | Cho et al. |
| 2015/0324546 A1 | 11/2015 | Dakshanamurthy et al. |
| 2016/0330018 A1 | 11/2016 | Miyato et al. |

FOREIGN PATENT DOCUMENTS

WO 2014011633 1/2014

OTHER PUBLICATIONS

Li, Wenfa, et al. "Supporting regularized logistic regression privately and efficiently." PloS one 11.6 (2016): e0156479.*
Cheng, Feixiong, et al. "Prediction of drug-target interactions and drug repositioning via network-based inference." PLoS Comput Biol 8.5 (2012): e1002503.*
Wikipedia: "Secret Sharing" as downloaded from https://en.wikipedia.org/wiki/Secret_sharing#Trivial_secret_sharing on Apr. 9, 2021.*
International Search Report and Written Opinion, PCT/US2018/06739, dated Apr. 29, 2019.
Catrina, et al., "Secure computation with fixed-point numbers," Financial Cryptography and Data Security, FC2010, LNCS 6052, 2010.
Luo, et al., "A network integration approach for drug-target interaction prediction and computational drug repositioning from heterogeneous information," Nature Communications, vol. 9, Article No. 573, Sep. 18, 2017.
Mohassel, et al., "SecureML: A system for scalable privacy-preserving machine learning," 2017 IEEE Symposium on Security and Privacy, May 2017.
Supplemental European Search Report and Search Opinion, EP Application No. 18 89 6915.8, dated Aug. 11, 2021.
Chase, et al., "Private Collaboration Neural Network Learning," IACR, vol. 20170808:183434, Aug. 7, 2017.
Riazi, et al., "Chameleon: A Hybrid Secure Computation Framework for Machine Learning Applications," IACR, vol. 20171130:2343054, Nov. 30, 2017.
Lan, et al., "A Distributed and Privatized Framework for Drug-Target Interaction Prediction," 2016 IEEE International Conference on Bioinformatics and Biomedicine (BIBM), Dec. 15, 2016.

* cited by examiner

*Primary Examiner* — G Steven Vanni
(74) *Attorney, Agent, or Firm* — David H. Judson

(57) ABSTRACT

Computationally-efficient techniques facilitate secure pharmacological collaboration with respect to private drug target interaction (DTI) data. In one embodiment, a method begins by receiving, via a secret sharing protocol, observed DTI data from individual participating entities. A secure computation then is executed against the secretly-shared data to generate a pooled DTI dataset. For increased computational efficiency, at least a part of the computation is executed over dimensionality-reduced data. The resulting pooled DTI dataset is then used to train a neural network model. The model is then used to provide one or more DTI predictions that are then returned to the participating entities (or other interested parties).

16 Claims, 5 Drawing Sheets

$[W]^{(f)}, [b]^{(f)} \leftarrow \text{GradientDescent}([X_{batch}]^{(f)}, [y_{batch}]^{(f)}, [W]^{(f)}, [b]^{(f)})$

Require: Mini-batch features $X_{batch} \in \mathbb{R}^{M_{batch} \times N}$, label vector $y_{batch} \in \{-1, +1\}^{M_{batch}}$, weight parameters W, bias parameters b, and velocity parameters $W_V$ and $b_V$.

/* Forward propagation. */
for $l = 1, ..., L$ do
    if $l = 1$ then
        $[Z^{(1)}]^{(f)} \leftarrow \text{Truncate}([W^{(1)}]^{(f)}[X_{batch}]^{(f)}, k + f, f)$
    else
        $[Z^{(1)}]^{(f)} \leftarrow \text{Truncate}([W^{(l)}]^{(f)}[Z^{(l-1)}]^{(f)}, k + f, f)$
    end if
    for $i = 1, ..., M$
        $\left[Z_{i,j}^{(l)}\right]^{(f)} \leftarrow \left[Z_{i,j}^{(l)}\right]^{(f)} + [b^{(l)}]^{(f)}$
    end
    $[\mathbb{1}\{Z^{(l)} > 0\}] \leftarrow \text{IsPositive}([Z^{(l)}]^{(f)})$
    $[Z^{(l)}]^{(f)} \leftarrow [Z^{(l)}]^{(f)} \odot [\mathbb{1}\{Z^{(l)} > 0\}]$
end for if $L = 0$ then
    $[s]^{(f)} \leftarrow \text{Truncate}([W^{(1)}]^{(f)}[X_{batch}]^{(f)}, k + f, f)$
else
    $[s]^{(f)} \leftarrow \text{Truncate}([W^{(L+1)}]^{(f)}[Z^{(L)}]^{(f)}, k + f, f)$
end if
for $i = 1, ..., M$
    $[s_j]^{(f)} \leftarrow [s_j]^{(f)} + [b^{(L+1)}]^{(f)}$
end

/* Loss function evaluation. */

$[-s \odot y_{batch}]^{(f)} \leftarrow \text{Truncate}(-[s]^{(f)} \odot [y_{batch}]^{(f)}, k+f, f)$ $[1-s \odot y_{batch}]^{(f)} \leftarrow \text{CP2: } [-s \odot y_{batch}]^{(f)} + 1$ $[\mathbb{1}\{1-s \odot y_{batch}\}] \leftarrow \text{IsPositive}([1-s \odot y_{batch}]^{(f)})$ $\left[\dfrac{1}{M_{batch}} \mathbb{1}\{1-s \odot y_{batch}\}\right]^{(f)} \leftarrow \dfrac{1}{M_{batch}} [\mathbb{1}\{1-s \odot y_{batch}\}]$ $[\delta^{(L+1)}]^{(f)} \leftarrow \text{Truncate}(-[y_{batch}]^{(f)} \odot \left[\dfrac{1}{M_{batch}} \mathbb{1}\{1-s \odot y_{batch}\}\right]^{(f)}, k+f, f)$ /* Backpropagation. */ for $l = L+1, ..., 1$ do if $l = 1$ then

$\left[\dfrac{\delta J}{\delta W^{(1)}}\right]^{(f)} \leftarrow \text{Truncate}\left([\delta^{(1)}]^{(f)} \left[X_{batch}^T\right]^{(f)}, k+f, f\right)$ else

$\left[\dfrac{\delta J}{\delta W^{(l)}}\right]^{(f)} \leftarrow \text{Truncate}\left([\delta^{(l)}]^{(f)} \left[Z^{(l-1)T}\right]^{(f)}, k+f, f\right)$ $\left[W^{(l)T}\delta^{(l)}\right]^{(f)} \leftarrow \text{Truncate}\left([W^{(l)T}]^{(f)} [\delta^{(l)}]^{(f)}, k+f, f\right)$ $[\mathbb{1}\{Z^{(l-1)} > 0\}] \leftarrow \text{IsPositive}\left(\left[Z^{(l-1)T}\right]^{(f)}\right)$ $[\delta^{(l-1)}]^{(f)} \leftarrow \left[W^{(l)T}\delta^{(l)}\right]^{(f)} \odot [\mathbb{1}\{Z^{(l-1)} > 0\}]$ end if

$\left[\dfrac{\delta J}{\delta W^{(l)}}\right]^{(f)} \leftarrow \left[\dfrac{\delta J}{\delta W^{(l)}}\right]^{(f)} + \text{Truncate}(\lambda [W^{(l)}]^{(f)}, k+f, f)$ $\left[\dfrac{\delta J}{\delta b^{(l)}}\right]^{(f)} \leftarrow [\delta^{(l)}]^{(f)} \mathbf{1}$ end for

TO FIG. 4B

FROM FIG. 4A

```
/* Parameter updates. */
for l = 1, ..., L + 1 do
```
$$\left[\left(\mathbf{W}_V^{(l)}\right)_{prev}\right]^{(f)} \leftarrow \left[\mathbf{W}_V^{(l)}\right]^{(f)}$$

$$\left[\mathbf{W}_V^{(l)}\right]^{(f)} \leftarrow \text{Truncate}\left(\mu\left[\mathbf{W}_V^{(l)}\right]^{(f)} - \alpha\left[\frac{\delta J}{\delta \mathbf{W}^{(l)}}\right]^{(f)}, k+f, f\right)$$

$$[\mathbf{W}^{(l)}]^{(f)} \leftarrow [\mathbf{W}^{(l)}]^{(f)} + \text{Truncate}\left(-\mu\left[(\mathbf{W}_V^{(l)})_{prev}\right]^{(f)} + (\mu+1)\left[\mathbf{W}_V^{(l)}\right]^{(f)}, k+f, f\right)$$

$$\left[\left(\mathbf{b}_V^{(l)}\right)_{prev}\right]^{(f)} \leftarrow \left[\mathbf{b}_V^{(l)}\right]^{(f)}$$

$$\left[\mathbf{b}_V^{(l)}\right]^{(f)} \leftarrow \text{Truncate}\left(\mu\left[\mathbf{b}_V^{(l)}\right]^{(f)} - \alpha\left[\frac{\delta J}{\delta \mathbf{b}^{(l)}}\right]^{(f)}, k+f, f\right)$$

$$[\mathbf{b}^{(l)}]^{(f)} \leftarrow [\mathbf{b}^{(l)}]^{(f)} + \text{Truncate}\left(-\mu\left[(\mathbf{b}_V^{(l)})_{prev}\right]^{(f)} + (\mu+1)\left[\mathbf{b}_V^{(l)}\right]^{(f)}, k+f, f\right)$$

```
end for
return [W]^(f), [b]^(f)
```

FIG. 4B

REALIZING PRIVATE AND PRACTICAL PHARMACOLOGICAL COLLABORATION USING A NEURAL NETWORK ARCHITECTURE CONFIGURED FOR REDUCED COMPUTATION OVERHEAD

TECHNICAL FIELD

This application relates generally to data sharing and collaboration in biomedicine.

BACKGROUND

Pharmaceutical companies and other biomedical researchers are painstakingly generating large datasets of drug compounds and linking them to potential targets of interest. While combining an unprecedented amount of data from multiple entities would power innovation and life-saving breakthroughs, open sharing of pharmacological data is generally not viable due to data privacy and intellectual property concerns.

In particular, computational prediction of drug-target interactions (DTIs) allows biomedical researchers to prioritize downstream experiments and accelerate pharmaceutical research. Recent advances in high-throughput screening (HTS) technologies have given rise to unprecedented amounts of DTI data which offer new opportunities for in silico DTI prediction. However, the space of chemical compounds with potential therapeutic effects and the space of potential targets in the post-genomic era are far too expansive to be experimentally interrogated in an exhaustive manner, even with HTS. In practice, individual laboratories observe only a small fraction of the landscape of possible DTIs. As pharmacological research pipelines face declining productivity and increasing calls for greater collaboration, jointly leveraging such data from across the pharmaceutical industry and academia could enable more accurate predictive models of DTIs and spur life-saving biomedical discoveries. However, pharmacological data is often tightly coupled with financial interests and therefore rarely shared. In particular, researchers may wish to maintain the confidentiality of new compounds under development or even the set of potential targets being tested, both of which may also contain sensitive information about underlying experimental strategies.

BRIEF SUMMARY

This disclosure provides for a secure and scalable cryptographic pipeline for pharmacological collaboration where multiple entities securely combine their data to jointly predict drug-target interactions with state-of-the-art accuracy. To this end, the subject matter herein is a computational protocol for drug-target interaction (DTI) prediction that is privacy-preserving, scales to millions of interactions, and achieves state-of-the-art prediction accuracy. Preferably, cryptographic tools are used to enable DTI data sharing that provably ensures the confidentiality of the underlying drugs, targets, and observed interactions. Preferably, this joint dataset is used to securely train a neural network model with predictive capabilities beyond that of any individual entity, without disclosing the original data to any of the involved parties. The end-to-end protocol identifies novel DTIs with strong clinical or experimental support and can train within days over a wide area network on a dataset with millions of observed interactions. The secure DTI prediction protocol lays the foundation for a transformational paradigm that enables more effective and collaborative biomedical research.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which:

FIG. 3, and FIGS. 4A and 4B together depict a preferred Gradient Descent algorithm for training a neural network according to an embodiment of this disclosure.

DETAILED DESCRIPTION

Modern cryptography offers techniques to encourage pharmacological collaboration by greatly mitigating privacy concerns associated with data sharing. For instance, secure multiparty computation (MPC) protocols allow multiple entities to securely compute over their private datasets without revealing any information about the underlying raw data, except for the final computational output. Unfortunately, the promise of privacy-preserving collaboration has been severely hindered by the inability of existing secure computation frameworks to scale to complex computations over large datasets, and in particular to DTI prediction on datasets with millions of interactions. This disclosure addresses this problem.

Figure 1:
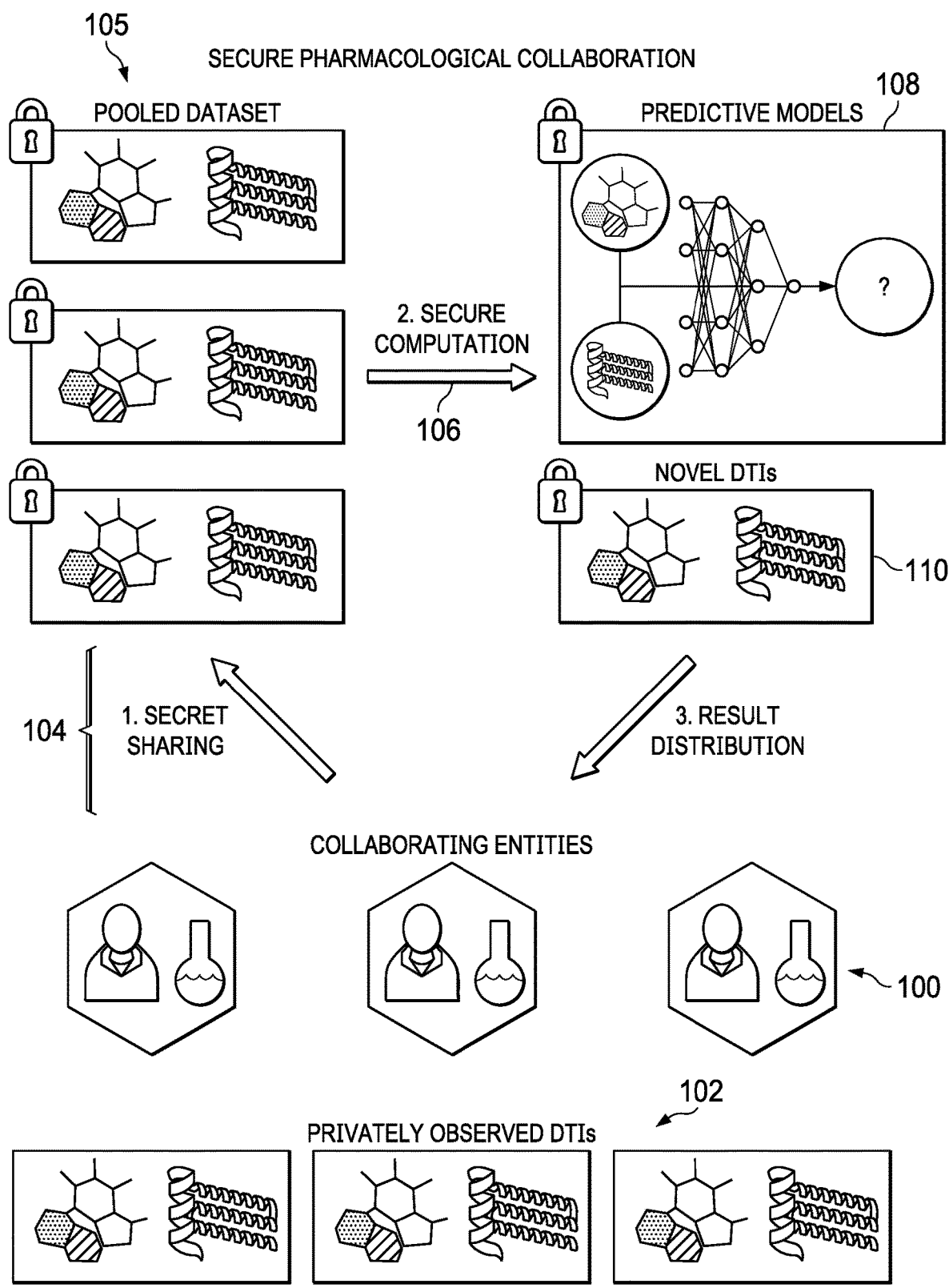
FIG. 1 is a multi-computing entity implementation environment in which the techniques of this disclosed may be practiced.

In particular, this disclosure provides for an end-to-end pipeline for collaborative DTI prediction based on secure MPC that newly enables privacy-preserving collaboration within practical runtimes even for million-interaction datasets. FIG. 1 depicts the basic framework. Conceptually, the protocol divides computation across collaborating entities while ensuring that none of the entities has any knowledge about the private data. This is achieved using a cryptographic framework known as secret sharing in which a private value ("secret") is collectively represented by multiple entities, where preferably each entity is given a random number ("share") in a finite field (i.e., integers modulo some prime number p) such that the sum of all shares modulo p equals the secret. Importantly, any strict subset of entities cannot extract any information about the underlying secret using their shares. Various protocols have been developed for performing elementary operations (e.g., addition, multiplication) over secret-shared inputs, which taken together form the building blocks for a general purpose MPC framework that performs arbitrary computation over secret-shared data without leaking any information about the private input.

While secret sharing-based MPC typically requires overwhelming amounts of data communication between entities for complex and large-scale computations, very recent optimizations have leveraged techniques, such as generalized Beaver triples and shared pseudorandom number generators (PRGs), to significantly reduce communication cost, enabling practical secure computation for challenging problems such as genome-wide association studies for a million individuals. Even with these advances, however, secure MPC may not be feasible for most DTI prediction methods that use matrix factorization or network diffusion to generalize the topology of the DTI network. This is primarily because these prediction methods scale quadratically with the number of drugs (n) and the number of targets (m) in the dataset (e.g., $n^2$ or nm), which is prohibitive for realistic datasets with millions of compounds. Although a recently proposed method for privacy-preserving matrix factorization obtains linear complexity in the number of observed interactions, it does not admit additional features known as "side information," which is important achieving competitive prediction performance. Moreover, without a sophisticated consideration of side information, matrix factorization has difficulty generalizing to drugs or proteins not in its training set, referred to as the "cold start problem."

To achieve scalable computation while admitting side information, according to this disclosure the input data preferably is represented as a list of observed DTIs, where each instance typically includes interaction score and feature vectors representing the drug and target side information, preferably all of which is then secretly-shared. A predictive model (which takes the feature vectors as input and outputs a predicted interaction score) is then trained, preferably by making linear passes over the DTIs, using each data instance to securely update the model parameters. This approach scales linearly with the number of observed DTIs, which is typically much smaller than the number of possible DTIs. Furthermore, the described approach results in a predictive model that naturally generalizes to previously unseen drugs or targets, unlike matrix factorization. In this protocol, preferably a neural network model is utilized due to its effectiveness in capturing complex patterns in the data.

Despite linear-time asymptotics, a naïve implementation of neural network training still incurs a high cryptographic overhead in MPC. To achieve practical runtimes, and according to this disclosure, a preferred architectural design is provided that specifically takes advantage of MPC operations that benefit from a reduced amount of computation. Computing neuron activations using a highly non-linear function like sigmoid or tan h is difficult to efficiently approximate in MPC; instead, the approach herein preferably uses a rectified linear unit (ReLU), because evaluating the ReLU and its derivative requires just a single data-oblivious comparison. Similarly, instead of less-efficient but more common alternatives such as cross entropy loss, preferably training scores are evaluated with hinge loss, which requires a single data-oblivious comparison. Preferably, and as will be described, training is accelerated using a mini-batch stochastic gradient descent, e.g., with Nesterov momentum. These techniques allow the secure neural network to train, preferably over a wide area network (WAN) in a relatively short time period (e.g., measured in hours or days), even with respect to a large dataset (e.g., with more than a million training instances). The MPC protocols as described herein readily generalize to other machine learning models, e.g., a secure support vector machine.

In one embodiment, multiple participating entities contribute secret-shared data to train a neural network on a joint DTI dataset, such as depicted in FIG. 1. After training, the model is made available to one or more (or all) participants, or the model could remain private such that entities receive a number of predictions commensurate with the amount of data they contribute, thereby further incentivizing participation. The more training data used, the better the performance, thereby entities are incentivized to share information in a way that is mutually beneficial but that still maintains privacy guarantees.

The pipeline is secure under an "honest-but-curious" security model in which the collaborating entities follow the correct protocol and do not collude to reconstruct the data. This approach is a substantial improvement over the current state of biomedical research where privacy concerns hinder any collaboration, and the framework can be extended to achieve even stronger security guarantees. In particular, because (as described below) the security guarantee holds as long as at least one entity is honest during the main computation, the no-collusion requirement can be related by introducing additional entities into the protocol. This alternative embodiment does not substantially increase total computation time but does increase communication linearly in the number of entities. Further, if additional security against malicious entities who deviate from the protocol during the online computation is required, a message authentication code (MAC) is included with each message, where at the end of the protocol the MAC is verified to ensure that each step was performed according to the protocol specification, a known technique. This alternative approach roughly doubles computation and communication, offering a tradeoff between security and performance that can be adjusted according to specific study requirements.

While the pipeline does not consider adding noise to the final computation output to limit information leakage, a technique known as differential privacy (methods currently being developed for differentially private neural networks) can be used in conjunction with the protocol. An alternative strategy for collaborative deep learning is to train local models in plaintext and to use secure protocols only when periodically averaging over these models, thus minimizing the amount of cryptographic overhead. The latter approach, however, is vulnerable to reverse engineering-based attacks in which a malicious collaborator jointly trains a local model (e.g., a generative adversarial network) that uncovers information about private data owned by honest collaborators, even when differential privacy techniques are applied. In contrast, securely training a single model over a decentralized network of computing parties, as in the preferred embodiment of the below-described pipeline, is not vulnerable to such attacks.

The privacy-preserving protocols described herein generalize to other large-scale data sharing problems beyond DTI prediction, with the highest potential for impact in areas that suffer from a lack of collaboration due to privacy concerns, such as predictive analyses of electronic health records. The secure DTI protocol as described herein enables greater scientific collaboration that realizes immense biological, commercial, and clinical benefit.

As depicted in FIG. 1, collaborating entities (e.g., pharmaceutical companies, research laboratories, and the like) 100 have large private datasets 102 of drug-target interactions (DTIs), as well as corresponding chemical structures and protein sequences. In one embodiment of the protocol, the entities first use secret sharing 104 to pool their data 105 in a way that reveals no information about the underlying drugs, targets, or interactions (step 1). The collaborating entities then jointly execute a cryptographic protocol 106 that trains a predictive model 108 (e.g., a neural network) on the pooled dataset (step 2). The final model can be made available to participating entities, or be used to distribute novel DTI predictions 110 to participants in a way that encourages greater data sharing (step 3).

Figure 2A:
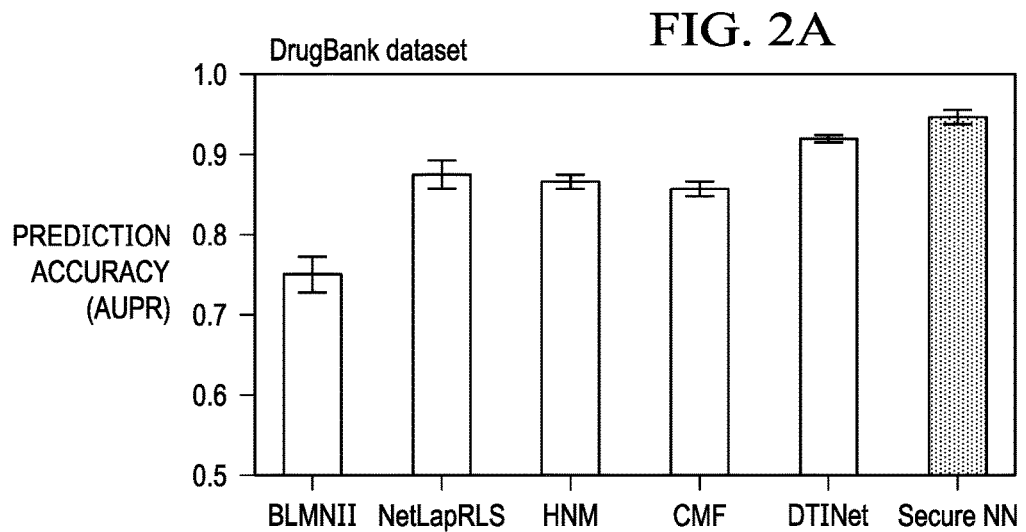
FIG. 2 depicts another view of the secure GWAS pipeline according to the techniques of this disclosure.
Figure 2B:
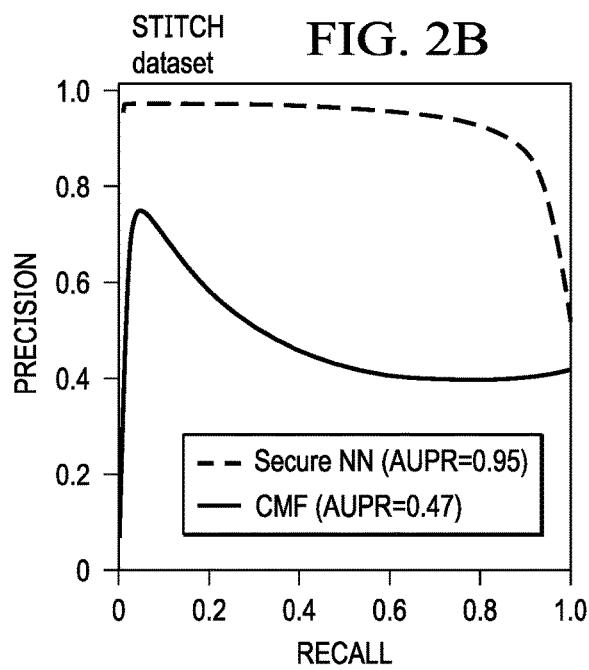
Figure 2C:
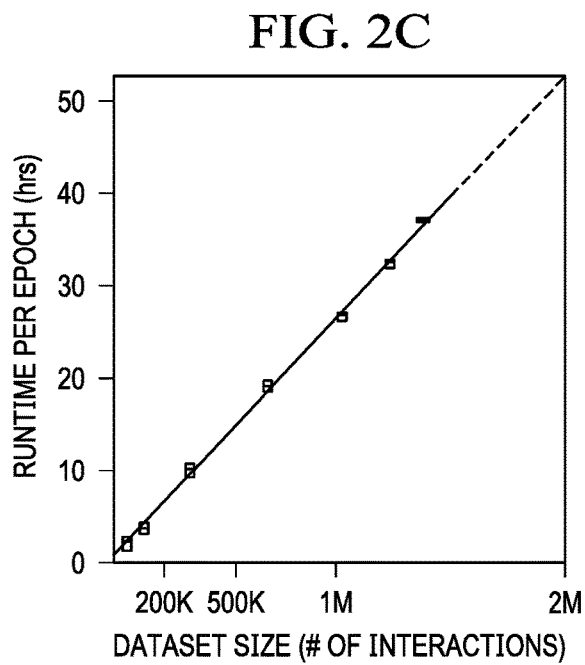

As depicted in FIG. 2, a secure neural network trained as described herein accurately predicts drug-target interactions within practical and scalable runtimes. In particular, graph (a) depicts the secure neural network (called "Secure NN") outperforming previous methods for DTI prediction on the DrugBank 3.0 dataset using 10-fold cross validation (CV) on balanced training and test sets. In this graph, bar height corresponds to mean AUPR (area under the precision-recall curve) and error bars correspond to the standard deviation. The methods compared include BLMNII, NetLapRLS, HNM, CMF, and DTINet. The graph (b) depicts that on a large-scale benchmark dataset with 1,357,742 drug-target pairs (the STITCH dataset), the Secure NN produces high quality predictions even when the test set consisted only of previously unseen chemicals and also outperforms plaintext CMF—the only baseline method which could be feasibly run on a dataset of this size. The graph (c) depicts the runtime of the training protocol, over a local area network (LAN), for different dataset sizes and observe a linear dependence, as expected. Box height represents the standard deviation. Even training on two million interactions, the total runtime for one epoch (one linear pass over the full, shuffled training set) is around 2.2 days. In practice, the model achieves high accuracy in only a few training epochs, e.g., after 1.5 epochs.

In one embodiment, the Secure NN is trained on all human drug-target interactions from the STITCH 5 database. The neural network is then used to score and rank the drug-target pairs that make up a remaining interaction space. Out of the top 20 interactions, excluding pairs with over-represented drugs and targets, almost all have strong clinical or experimental support for interactivity, and some top-ranked pairs are considered to represent novel interactions.

Overview of Steps for Secure Neural Network Computation

For this description, consider the simplest setting with two collaborating entities (e.g., academic labs or pharmaceutical companies), denoted CP1 and CP2 ("computing parties"). Typically, the protocol also involves a third auxiliary entity CP0 that is involved, but preferably only during an offline pre-computation phase. Entity CP0 cannot collude with other entities in the protocol (for the security guarantee to hold), thus CP0 is a trusted party. Using a cryptographic technique called secret sharing, each of CP1 and CP2 shares its DTI data (i.e., drug- and target-specific input features and observed interaction scores) with the other participant in such a way that enables privacy-preserving computation over the pooled data. During this computation, CP1 and CP2 preferably leverage pre-computed data from CP0 (which is input-agnostic) to greatly speed up the computation. A preferred technique to this end is generalized Beaver partitioning. CP1 and CP2 then combine their outputs to reconstruct the final results (e.g., neural network weights or predicted DTIs).

As noted above, the approach herein adopts the "honest-but-curious" security model in which the protocol participants are assumed to follow the protocol exactly as specified, but at the end of the protocol execution, a party may try to infer additional information about other parties' private inputs based on their view of the protocol. Under this setting, the protocol herein is secure as long as CP0 and at least one of the other CPs remains honest. In a preferred embodiment, all communication occurs over a secure and authenticated channel (e.g., over the TLS protocol).

Preferably, the protocol relies on a two-party additive secret sharing scheme where a value $x \in \mathbb{Z}_q$ is shared between CP1 and CP2, where a secret sharing of x between CP1 and CP2 is denoted as $[x] \triangleq \langle [x]_1, [x]_2 \rangle$, where the notation $\langle [x]_1, [x]_2 \rangle$ means that $[x]_1$ and $[x]_2$ are shares of x in $\mathbb{Z}_q$ individually owned by CP1 and CP2, respectively, such that $x=[x]_1+[x]_2$. Adding two secret shared values $[x]$ and $[y]$ can be done by having each party add their own shares, i.e., $\langle [x]_1+[y]_1, [x]_2+[y]_2 \rangle$. Adding by a public field element $a \in \mathbb{Z}_q$ can be written as $\langle [x]_1+a, [x]_2 \rangle$. Multiplying by a public field element is also simple and can be written as $\langle a[x]_1, a[x]_2 \rangle$. Multiplying two secret shared values is more involved but preferably leverages Beaver multiplication triples for efficiently computing many multiplications, including matrix multiplications. Preferably, the protocol uses a fixed-point representation of signed real numbers that uses k total bits, of which f is the number of bits allocated to the fractional domain, referred to as the "precision." We denote a secret shared fixed-point encoding of $x \in \mathbb{R}$ as $[x]^{(f)}$. Multiplication of two fixed point numbers outputs a result with precision of 2f instead of f, so preferably a truncation routine is used to rescale the precision, which is denoted $$[x_{trunc}] \leftarrow \text{Truncate}([x], b, s)$$

where b is the number of bits to mask, which is chosen such that a sufficient level of statistical security is guaranteed, and s is the number of least significant bits to truncate. Preferably, the protocol uses a data oblivious sign test (i.e., a comparison with zero) that takes the form $$[\mathbb{1}\{x>0\}] \leftarrow \text{IsPositive}([x]^{(f)})$$

where $[\mathbb{1}\{x>0\}]$ is a secret shared integer value equal to 1 if x is positive, and 0 otherwise. This comparison protocol requires $O(1)$ rounds of computation and $O(k)$ invocations of multiplication protocols, where k is the bit length.

A preferred neural network model as used herein is now defined. The technique assumes a feature matrix $X \in \mathbb{R}^{N \times M}$, where each row corresponds to a single training example and each column corresponds to a single data feature. The technique also assumes a label vector $y \in \{-1, +1\}^M$ where $y_i=+1$ if $X_{:,i}$ is a positive training example and $y_i=-1$ otherwise. While binary labels are assumed, the framework generalizes to continuous interaction scores. Preferably, the neural network model is a standard multilayer perceptron, consisting of real-valued weight matrices $W^{(1)}, \ldots, W^{(L+1)}$ and column vector biases $b^{(1)}, \ldots, b^{(L+1)}$, where L is the number of hidden layers and where each hidden layer consists of neurons $Z^{(1)}, \ldots, Z^{(L)}$. During a forward-propagation phase, certain neurons are "activated" according to $$Z_{:,i}^{(1)} = f_{act}(W^{(1)} X_{:,i} + b^{(1)}) \text{ and}$$

$$Z_{:,i}^{(l)} = f_{act}(W^{(l)} Z_{:,i}^{(l-1)} + b^{(l-1)})$$

for $l=2, \ldots, L$ and $i=1, \ldots, M$. For present purposes, it is assumed that each hidden layer has the same number of neurons, denoted H, where $Z^{(l)} \in \mathbb{R}^{H \times M}$. The function $f_{act}$ is known as an activation function, which in the neural network is the rectified linear unit (ReLU), which takes the form $f_{act}(x)=\max\{0, x\}$. After the final hidden layer, the model outputs scores $s \in \mathbb{R}^M$ where $$s_i = W^{(L+1)} Z_{:,i}^{(L)} + b^{(L+1)}$$

for $i=1, \ldots, M$. Note that in a single output setting, $W^{(L+1)} \in \mathbb{R}^{1 \times H}$ and $b^{(L+1)} \in \mathbb{R}$. Preferably, the predictive performance of the model is evaluated using the hinge loss function, $$\mathcal{J}(s, y) = \frac{1}{M} \sum_{i=1}^{M} \max\{0, 1 - s_i y_i\},$$

where $\odot$ is the component-wise (or Hadamard) product. Next, these errors are used to compute derivative updates to the weights and biases, starting with the output layer, where $$\delta^{(L+1)T} = y \odot \frac{1}{M} \mathbb{1}\{1 - s \odot y > 0\},$$

$$\frac{\partial \mathcal{J}}{\partial W^{(L+1)}} = \delta^{(L+1)} Z^{(L)T} + \lambda W^{(L+1)}, \text{ and}$$

$$\frac{\partial \mathcal{J}}{\partial b^{(L+1)}} = \delta^{(L+1)} 1.$$

Note that a regularization term is added to the weight updates parameterized by the constant $\lambda$.

Following a standard backpropagation algorithm for training neural networks, these derivatives are recursively propagated through each hidden layer using $$\delta^{(l)} = \left(W^{(l+1)T} \delta^{(l+1)}\right) \odot \mathbb{1}\{Z^{(l)} > 0\},$$

$$\frac{\partial \mathcal{J}}{\partial W^{(l)}} = \delta^{(l)} Z^{(l-1)T} + \lambda W^{(l)}, \text{ and}$$

$$\frac{\partial \mathcal{J}}{\partial b^{(l)}} = \delta^{(l)} 1$$

for hidden layers $l=2, \ldots, L$ and for the input layer $l=1$, $$\frac{\partial \mathcal{J}}{\partial W^{(1)}} = \delta^{(1)} X^T + \lambda W^{(1)} \text{ and } \frac{\partial \mathcal{J}}{\partial b^{(1)}} = \delta^{(1)} 1.$$

Finally, the model weights and biases are updated, e.g., using Nesterov momentum updates $$\Theta_v^{(t+1)} = \mu \Theta_v^{(t)} - \alpha \frac{\partial \mathcal{J}}{\partial \Theta^{(t)}},$$

$$\Theta^{(t+1)} = \Theta^{(t)} - \mu \Theta_v^{(t)} + (1 + \mu) \Theta_v^{(t+1)}$$

for parameters $\Theta \in \{W^{(1)}, \ldots, W^{(L+1)}, b^{(1)}, \ldots, b^{(L+1)}\}$, successive time steps $t=1, \ldots, T$, and constants $\mu$ and $\alpha$ which are the momentum and learning rates, respectively. Preferably, Nesterov momentum is used instead of standard momentum because it has better convergence guarantees for convex functions.

In practice, it is not required to use all training examples for each parameter update iteration; rather, it is sufficient to use a random subset referred to as a "mini-batch," which is denoted $X_{batch} \in \mathbb{R}^{N \times M_{batch}}$ and the corresponding labels $y_{batch} \in \{-1, +1\}^{M_{batch}}$. In one embodiment of the protocol, $X_{batch}$ and $y_{batch}$ are sampled randomly without replacement until all training examples have been considered, after which all training data is restored, and the process repeated. Preferably, these randomly sampled mini-batches are used to iteratively compute the unbiased estimate of the gradient and update the model parameters, a procedure referred to as stochastic gradient descent (SGD).

In particular, the following defines a secure protocol for neural network training. First, a GradientDescent protocol is implemented, which protocol takes as input $[X_{batch}]^{(f)}$, $[y_{batch}]^{(f)}$, $$[W]^{(f)} = \{[W^{(1)}]^{(f)}, \ldots, [W^{(L+1)}]^{(f)}, [W_v^{(1)}]^{(f)}, \ldots, [W_v^{(L+1)}]^{(f)}\}, \text{ and}$$

$$[b]^{(f)} = \{[b^{(1)}]^{(f)}, \ldots, [b^{(L+1)}]^{(f)}, [b_v^{(1)}]^{(f)}, \ldots, [b_v^{(L+1)}]^{(f)}\},$$

and then outputs the updated model parameters $[W]^{(f)}$ and $[b]^{(f)}$ after performing a single stochastic gradient update.

FIG. 3, together with FIGS. 4A and 4B, depict a preferred GradientDescent protocol in detail. This protocol preferably is implemented in software executing in hardware. Preferably, multiple rounds of GradientDescent are invoked in which a new and $X_{batch}$ corresponding $y_{batch}$ are randomly sampled from the full dataset, which is repeated until reaching the max number of iterations T. Finally, after the training procedure is finished, the two collaborating entities CP1 and CP2 preferably combine their shares to jointly reconstruct $W^{(1)}, \ldots, W^{(L+1)}$ and $b^{(1)}, \ldots, b^{(L+1)}$ in plaintext.

In a representative embodiment, the neural network model (e.g., for the STITCH dataset experiments) has hyper-parameters N=6903, $M_{batch}$=100, L=2, H=50, T=20,000, $\lambda$=0.001, $\mu$=0.9, and $\alpha$=0.005. Hyperparameters preferably are chosen based on a grid search (in plaintext) of around 10 different hyperparameter combinations. The model performance is robust to a wide range of hyperparameter settings. In addition, with the same parameter tuning methodology in a secure WAN setting, the tuning phase can be sped up with parallelism and other coordinated tuning strategies.

As an alternative to a neural network, a linear-kernel Support Vector Machine (SVM) may be used. The MPC protocol for the secure neural network and SVM may be implemented in C++ based on the number theory package NTL version 10.3.0 for finite field operations. Other data processing scripts are implemented in Python and the NumPy package. Representative computing systems include CP1: 2.40 GHz Intel Xeon E5-2695v2 CPU with 384 GB RAM, CP2: 2.30 GHz Intel Xeon E5-2650v3 CPU with 384 GB RAM; and CP0: 3.33 GHz Intel Xeon X5680 CPU with 96 GB RAM.

One or more functions of the computing platform of this disclosure may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct. Communication networks used to communicate to and from the platform services may be packet-based, non-packet based, and secure or non-secure, or some combination thereof.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines.

A computing entity herein receives the secretly-shared data from a client device, which may even be an end user device. Thus for example, but without limitation, a client device is a mobile device, such as a smartphone, tablet, or wearable computing device. Such a device comprises a CPU (central processing unit), computer memory, such as RAM, and a drive. The device software includes an operating system (e.g., Google® Android™, or the like), and generic support applications and utilities.

The underlying network transport may be any communication medium including, without limitation, packet-based, cellular, wireless, Wi-Fi, small cell, and combinations thereof.

Each above-described process (e.g., each of the protocols set forth in the drawings) preferably is implemented in computer software as a set of computer program instructions executable in one or more processors, as a special-purpose machine.

Representative machines on which the subject matter herein is provided may be hardware processor-based computers running an operating system and one or more applications to carry out the described functionality.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system, such as Linux. A machine implementing the techniques herein comprises a hardware processor, and non-transitory computer memory holding computer program instructions that are executed by the processor to perform the above-described methods.

Communications herein (e.g., secret sharing of data, sharing of PRGs, etc.) preferably take place over secure connections. For machine-to-machine communications over a network, information typically is communicated over SSL/TLS links, or using any other protocol, although if significant trust is in place (e.g., machines being operated in a secure environment, or between entities that have a trust relationship, etc.) information may be transmitted in the clear. In lieu of using physically-distinct computing entities, computations herein may be carried out within a cluster comprises a set of computing entities (e.g., processors). A grid computing architecture may also be utilized.

There is no limitation on the type of computing entity that may implement any connection (e.g. client-to-server). Any computing entity (system, machine, device, program, process, utility, or the like) may act as a client or a server.

While given components of the system have been described separately, one of ordinary skill will appreciate that some of the functions may be combined or shared in given instructions, program sequences, code portions, and the like. Any application or functionality described herein may be implemented as native code, by providing hooks into another application, by facilitating use of the mechanism as a plug-in, by linking to the mechanism, and the like.

The functionality may be co-located or various parts/components may be separately and run as distinct functions, perhaps in one or more locations (over a distributed network). There may any number of computing parties that securely compute the DTI statistics using the secretly-shared data sets (namely, the data, and the random number data created during the pre-processing operation). The entity that performs pre-processing (CP0) may also be a computing entity (e.g., CP1) in the MPC computation to generate the DIT output.

The pre-processing may be provided as a service.

The secure computation may be provided as a service.

Computing entities herein may be independent from one another, or associated with one another. Multiple computing entities may be associated with a single enterprise entity, but are separate and distinct from one another with respect to the MPC secure computation itself over their respective secret shares.

The protocol may leverage several advanced computational techniques, which are now generally described. Details of these techniques are provided in U.S. Ser. No. 16/020,058, filed Jun. 27, 2018, the disclosure of which is hereby incorporated by reference. One technique improves upon an existing building block for secure computation, known as Beaver triples. Beaver triples were originally developed for carrying out secure pairwise multiplications; they are extended to arbitrary arithmetic circuits to thereby obtain more efficient subroutines for various operations such as matrix multiplication and exponentiation. Another technique involves using a random projection-based algorithm for Principal Component Analysis (PCA) so that the scale of the data is greatly reduced. An additional technique provides for the notion of shared pseudorandom number generators (PRGs) between pairs of computing entities; the use of shared PRGs obviates transferring a stream of random numbers, which is a frequent operation in the protocol, by enabling each party to independently draw the random numbers from the same PRG. Collectively, these techniques (namely, improved secure computation building blocks, randomized PCA for population stratification, and shared PRGs) enable the provision of a secure protocol that achieves practical scalability.

These computational techniques leverages building blocks that enable arbitrary arithmetic functions, i.e., addition and multiplication, over the private input, to be securely evaluated. The preferred approach avoids the requirement of generating a Beaver triple for every pairwise multiplication, which is computationally-inefficient especially if the overall computation contains many multiplications. As mentioned above, preferably the MPC technique with elements in a finite field, and there are additional high-level routines for various bit operations like bit shift, bit comparison, etc., which preferably are also written as arithmetic functions so that they can be efficiently-implemented. To address the problem (of having to generate a Beaver triple for every pairwise multiplication), the approach generalizes Beaver triples so that auxiliary random numbers, which enable the secure evaluation of nonlinear functions, are generated for groups of operations at a time, rather than for each individual multiplication. In particular, the generalized Beaver tuple preferably includes a random number for each input value, and some function of these random numbers for each of the output values of a desired computation. Thus, in this operation-centric to data-centric view, the total amount of auxiliary data to be generated and secret-shared depends on the size of input and output, rather than the number of pairwise multiplications, and this leads to significant computational efficiency. Although there are many ways to generate the Beaver triple, according to the protocol (and as noted above) preferably a third party (CP0) is used to perform this task. As noted, the third-party preferably does not observe the input data in any way and is able to finish its task before the main protocol, as a pre-processing step.

The technical advances in achieving a scalable MPC protocol for realizing private and practical pharmacological collaboration as described herein may be extended for use with diverse applications in biomedicine and other disciplines. The computational approach herein allows pharmaceutical companies and academic researchers (and other interested parties) to pool their data for more accurate predictions while keeping the raw data private. Further, the methods for secure computation removes obstacles for data sharing and, as a result, enable new workflows and opportunities for improved scientific collaboration.

The invention claimed is:

1. A method for pharmacological collaboration, comprising:
    receiving, via secret sharing, drug target interaction (DTI) data of individual collaborating entities and thereby generating a pooled DTI dataset, wherein the secret sharing preserves privacy of individual drugs, targets and interactions;
    training a neural network by executing multiple passes over the pooled DTI dataset, wherein the neural network comprises a rectified linear unit (RELU) activation function, and wherein parameters of the neural network are securely updated after a given pass;
    wherein the neural network is trained using stochastic gradient descent with Nesterov momentum; and
    wherein, during training, the neural network is evaluated using a hinge loss function;
    wherein the RELU activation and hinge loss functions are each evaluated using a single data-oblivious comparison, thereby reducing computation overhead;
    following training that occurs over a scalable runtime due at least in part to the reduced computation overhead, generating one or more DTI predictions for a drug discovery workflow using the neural network.

2. The method as described in claim 1 wherein the DTI data of at least one of the individual collaborating entities comprises drug and target side information, the drug and target side information including an interaction score, and one or more feature vectors.

3. The method as described in claim 2 wherein the DTI data further include chemical structures and protein sequences describing the drug.

4. The method as described in claim 1 wherein the individual collaborating entities comprise a first collaborating entity, and a second collaborating entity, wherein the first and second collaborating entities are independent from one another.

5. The method as described in claim 1 wherein the stochastic gradient descent with Nesterov momentum uses a random subset of the pooled DTI dataset.

6. The method as described in claim 1 wherein the secret sharing is carried out at least in part over a wide area network (WAN).

7. The method as described in claim 1 wherein the secret sharing is performed over a finite field.

8. The method as described in claim 1 further including distributing a given DTI prediction of the one or more DTI predictions.

9. The method as described in claim 8 wherein the given DTI prediction is distributed to one or more of the individual collaborating entities.

10. The method as described in claim 1 wherein the one or more passes are each a linear pass.

11. The method as described in claim 1 wherein the training scales linearly with respect to a subset of the DTI data.

12. The method as described in claim 1 wherein the DTI data comprises greater than $10^6$ drug target interactions and the training is executed over a time period measured in hours.

13. The method as described in claim 12 wherein the training is further executed over a wide area network (WAN).

14. A method for pharmacologic collaboration involving drug target interaction (DTI) data of two or more collaborating entities, the DTI data having been secretly shared to generate a pooled DTI dataset, wherein the secret sharing preserves privacy of individual drugs, targets and interactions, comprising:
    providing a neural network configured for reduced computation overhead by using a rectified linear unit (RELU) activation function, together with a hinge loss function that evaluates training scores, wherein each of the RELU activation and hinge loss functions use a single data-oblivious comparison, thereby reducing the computation overhead;
    training the neural network at least in part using stochastic gradient descent and with a random subset of training examples for at least one neural network parameter update iteration;
    following training that occurs over a scalable runtime due at least in part to the reduced computation overhead, generating one or more DTI predictions for a drug discovery workflow using the neural network.

15. The method as described in claim 14 wherein the DTI data comprises greater than $10^6$ drug target interactions and the training is executed over a time period measured in hours.

16. The method as described in claim 15 wherein the training is further executed over a wide area network (WAN).

* * * * *